United States Patent
Pelrine et al.

(10) Patent No.: US 10,861,627 B2
(45) Date of Patent: Dec. 8, 2020

(54) MICROROBOT AND MICROROBOTIC TRAIN SELF-ASSEMBLY WITH END-EFFECTORS

(71) Applicant: SRI INTERNATIONAL, Menlo Park, CA (US)

(72) Inventors: Ronald E. Pelrine, Longmont, CO (US); Annjoe Wong-Foy, Pacifica, CA (US); Allen L. Hsu, Mountain View, CA (US); Jose P. Joseph, Palo Alto, CA (US)

(73) Assignee: SRI International, Menlo Park, CA (US)

( * ) Notice: Subject to any disclaimer, the term of this patent is extended or adjusted under 35 U.S.C. 154(b) by 248 days.

(21) Appl. No.: 15/565,344

(22) PCT Filed: Apr. 20, 2016

(86) PCT No.: PCT/US2016/028448
§ 371 (c)(1),
(2) Date: Oct. 9, 2017

(87) PCT Pub. No.: WO2016/172217
PCT Pub. Date: Oct. 27, 2016

(65) Prior Publication Data
US 2018/0114621 A1    Apr. 26, 2018

Related U.S. Application Data

(60) Provisional application No. 62/149,891, filed on Apr. 20, 2015, provisional application No. 62/149,885, (Continued)

(51) Int. Cl.
*H01F 7/02* (2006.01)
*H01F 7/06* (2006.01)
(Continued)

(52) U.S. Cl.
CPC ......... *H01F 7/0242* (2013.01); *H01F 7/0236* (2013.01); *H01F 7/06* (2013.01);
(Continued)

(58) Field of Classification Search
CPC ......... H01F 7/0242; H01F 7/0236; H01F 7/06
See application file for complete search history.

(56) References Cited

U.S. PATENT DOCUMENTS

| | | |
|---|---|---|
| 3,597,022 A | 8/1971 | Waldron |
| 4,835,424 A | 5/1989 | Hoffman et al. |

(Continued)

FOREIGN PATENT DOCUMENTS

| | | |
|---|---|---|
| WO | 200168256 A3 | 9/2001 |
| WO | 2012075205 A1 | 6/2012 |

OTHER PUBLICATIONS

International Search Report dated Apr. 3, 2012 in corresponding International Application No. PCT/US11/62732.

(Continued)

*Primary Examiner* — Tuan V Nguyen
(74) *Attorney, Agent, or Firm* — McDonnell Boehnen Hulbert & Berghoff LLP

(57) ABSTRACT

A microrobot assembly system includes a substrate containing conductive traces formed into at least one holding zone and one moving zone, a diamagnetic layer on the substrate, at least two magnetic structures movable across the diamagnetic layer in response to voltages applied to the conductive traces, wherein the holding zone holds one of the magnetic structures and the moving zone allows another of the magnetic structures to attach to the magnetic structure being held. The system may include a plate spaced above the substrate and rails to guide the moving magnetic structures.

11 Claims, 4 Drawing Sheets

Related U.S. Application Data filed on Apr. 20, 2015, provisional application No. 62/162,514, filed on May 15, 2015, provisional application No. 62/296,638, filed on Feb. 18, 2016.

(51) Int. Cl.
  *A61B 10/02* (2006.01)
  *A61M 25/01* (2006.01)
  *B60L 13/04* (2006.01)

(52) U.S. Cl.
  CPC ...... *A61B 10/0233* (2013.01); *A61M 25/0127* (2013.01); *B60L 13/04* (2013.01)

(56) References Cited

U.S. PATENT DOCUMENTS

| | | | |
|---|---|---|---|
| 5,015,622 A | 5/1991 | Ward et al. |
| 5,193,267 A | 3/1993 | Satoh et al. |
| 5,298,875 A | 3/1994 | Laibowitz et al. |
| 5,396,136 A | 3/1995 | Pelrine |
| 5,783,915 A | 7/1998 | Shida et al. |
| 5,795,457 A | 8/1998 | Pethig et al. |
| 5,925,956 A | 7/1999 | Ohzeki |
| 5,955,800 A | 9/1999 | Shearwood et al. |
| 6,064,170 A | 5/2000 | Spurr et al. |
| 6,075,924 A | 6/2000 | Will |
| 6,097,114 A | 8/2000 | Hazelton |
| 6,175,169 B1 | 1/2001 | Hollis, Jr. et al. |
| 6,293,006 B1 | 9/2001 | Takeda et al. |
| 6,520,315 B1 | 2/2003 | Sugarman et al. |
| 6,703,768 B2 | 3/2004 | Kageyama |
| 6,858,184 B2 | 2/2005 | Pelrine et al. |
| 6,922,119 B2 | 7/2005 | Matsuta et al. |
| 7,084,532 B2 | 8/2006 | Widdowson et al. |
| 7,084,533 B2 | 8/2006 | Botos et al. |
| 7,126,134 B2 | 10/2006 | Lean et al. |
| 7,189,359 B2 | 3/2007 | Yuan et al. |
| 7,206,671 B2 | 4/2007 | Mizuno |
| 7,362,586 B2 | 4/2008 | Mashimo et al. |
| 7,847,824 B2 | 12/2010 | Mogamiya |
| 8,164,232 B2 | 4/2012 | Kornbluh et al. |
| 8,613,500 B2 | 12/2013 | Kobayashi |
| 2002/0020836 A1 | 2/2002 | Kikuchi et al. |
| 2002/0106314 A1 | 8/2002 | Pelrine et al. |
| 2003/0155821 A1 | 8/2003 | Frissen et al. |
| 2005/0194841 A1 | 9/2005 | Widdowson et al. |
| 2006/0078407 A1 | 4/2006 | Del Puerto et al. |
| 2006/0175910 A1 | 6/2006 | Asano et al. |
| 2007/0111117 A1 | 5/2007 | Noh et al. |
| 2008/0169712 A1 | 7/2008 | Koyama et al. |
| 2009/0002462 A1 | 1/2009 | Okawa et al. |
| 2010/0026443 A1 | 2/2010 | Yan et al. |
| 2014/0123461 A1 | 5/2014 | Whitesids et al. |
| 2014/0183979 A1 | 7/2014 | Pelrine et al. |
| 2014/0217835 A1 | 8/2014 | Pelrine et al. |
| 2014/0225694 A1* | 8/2014 | Sitti ............... H01F 13/003 335/295 |

OTHER PUBLICATIONS

International Search Report and Written Opinion, PCT/US2016/028448, dated Sep. 13, 2016.

European Search Report, dated Oct. 16, 2015, EP Patent Application No. 11844154.2, 6 pages.

\* cited by examiner

MICROROBOT AND MICROROBOTIC TRAIN SELF-ASSEMBLY WITH END-EFFECTORS

RELATED APPLICATIONS

This application is a § 371 U.S. National Stage of International Serial No. PCT/US2016/028448 filed Apr. 20, 2016, which claims priority to and the benefit of U.S. Provisional Application No. 62/149,885, filed Apr. 20, 2015, U.S. Provisional Application No. 61/149,891, filed Apr. 20, 2015, U.S. Provisional Application No. 62/162,514, filed May 15, 2015, and U.S. Provisional Application No. 62/296,638, filed Feb. 18, 2016, the contents of which are hereby fully incorporated by reference.

GOVERNMENT RIGHTS

This invention was made with Government support under contract HR0011-12-C-0040 awarded by Defense Advanced Research Projects Agency. The government has certain rights in this invention.

BACKGROUND

Microrobots, also referred to as micromanipulators, typically consist of an array of magnets that can move across a diamagnetic surface, such a graphite. A circuit substrate having conductive traces lies under the diamagnetic layer. When a controller applies voltages to the traces, the resulting magnetic fields control the movements of the microrobots. Aspects of these microrobots and associated systems are discussed in U.S. Pat. Nos. 8,593,016, 8,868,602, 8,941,270, and 6,858,184.

These microrobots provide a degree of flexibility and adaptability previously unattainable by micromanufacturing systems. In some instances, the microrobots having the ability to assemble and reconfigure themselves would provide even more flexibility in the applications that use them. For some applications, the microrobots alone do not transmit enough force to accomplish some desired tasks. If the microrobots had the ability not only to assemble themselves into microrobots from individual magnets, but to join with other microrobots, more applications would become possible.

Another aspect of the microrobot systems involve the tools, referred to as end effectors, that attach to the microrobots. The microrobots use the end effectors to manipulate other items, often in pick and place manufacturing systems. In current systems, some of the pickup end effectors do not hold the item effectively. Typically, the picking operation for small size objects uses wetting, but simpler wetting surfaces tend to dry out and one cannot easily determine if the end effector still has water. Other issues may arise because of surface rigidity.

SUMMARY

An embodiment includes a microrobot assembly system having a substrate containing conductive traces formed into at least one holding zone and one moving zone, a diamagnetic layer on the substrate, and at least two magnetic structures movable across the diamagnetic layer in response to voltages applied to the conductive traces, wherein the holding zone holds one of the magnetic structures and the moving zone allows another of the magnetic structures to attach to the magnetic structure being held.

Another embodiment is a microrobot including an array of magnets forming a body of a microrobots, an end effector having a capillary, and a wettable tip.

Another embodiment is a microrobot system including at least two microrobots, each microrobot having a front connector and a back connector and a tool end effector, wherein a first microrobot has a front connector connected to a back connector of a second microrobot, and an implement having a magnetic drive forming a forward path and a return path.

Another embodiment is a microrobot assembly system having a substrate containing at least one conductive trace, a diamagnetic layer on the substrate, at least one spacer on the diamagnetic layer having a predetermined height, a plate on the spacers, and at least two magnets movable across the diamagnetic layer when voltage is applied to the at least one conductive trace, the magnets having a height less than the predetermined height.

DETAILED DESCRIPTION OF THE EMBODIMENTS

Figure 1:
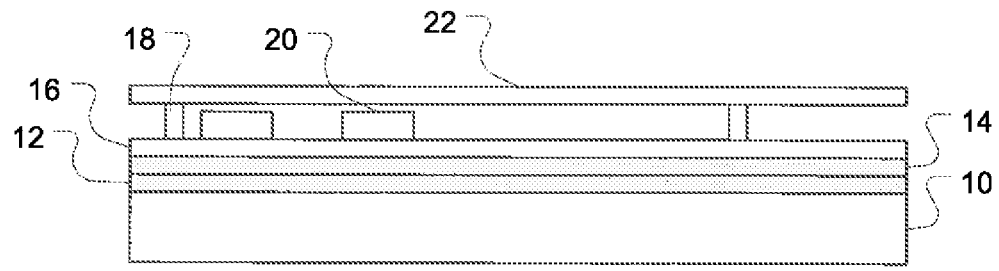
FIG. 1 shows a side view of a microrobot assembly system.

FIG. 1 shows a side view of a microrobot assembly system. In this embodiment, the microrobot assembly system includes a substrate 10. The substrate 10 may consist of a typical printed circuit board (PCB), ceramic, flex circuits, etc. The substrate has at least one layer of conductive traces such as 12. Typically, the substrate may contain multiple layers of conductive traces such as 12 and 14. When a controller applies voltage to these traces, the current flowing in the traces generates electromagnetic fields that can be used to control magnets.

The magnets, such as 20, used here are single-polarity magnets, meaning that they have a single direction of magnetization, that become microrobots when joined together. As will be discussed later, the microrobots can form trains of microrobots. This discussion refers to any of these structures as magnetic structures.

The substrate 10 has a diamagnetic layer 16 that allows the magnets to either move across the surface of the substrate with the diamagnetic layer, or even 'float' or levitate above the surface because of the magnetic fields. As will be discussed in more detail further, the magnets and microrobots can move vertically, so the plate 22 restrains the motion to prevent one of the magnets or microrobots from getting on top of the other. The plate 22 lies above the substrate a distance on spacers such as 18 sufficient to allow the magnets such as 20 to fit underneath the plate. The plate may consist of glass, aluminum, copper or any other planar material. The use of a metal plate may assist with damping eddy currents.

Figure 2:
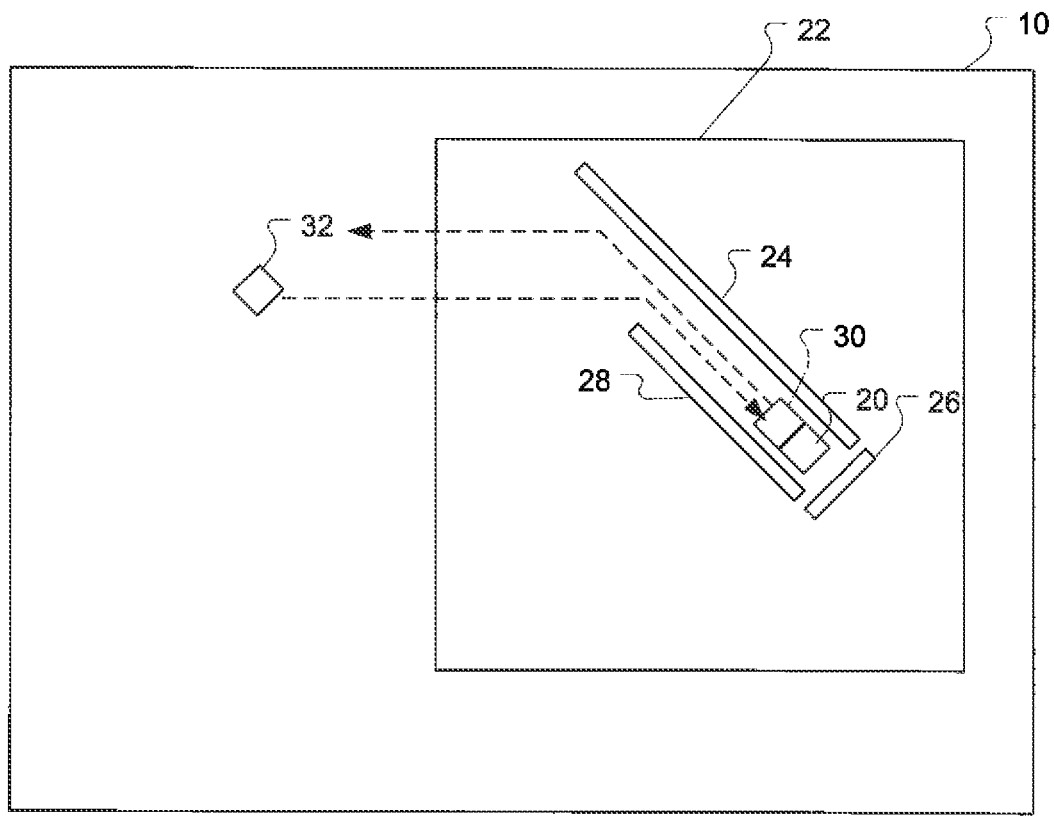
FIG. 2 shows a top view of an embodiment of a microrobot assembly system.

The basic system includes the substrate with conductive traces, a diamagnetic layer, the plate and the magnets that eventually form the microrobots. Several different configurations of the system are possible. In one embodiment, the spacers such as 18 may form guides to allow the magnets to be directed into an assembly area, or incubator. In the embodiment of FIG. 2, the incubator is formed by a mechanical stop 26, and two guides 24 and 28. Guide 24 acts as an error correcting guide that allows the magnet to be driven into the guide 24 and towards the mechanical stop 26. The magnets 20 and 30 have opposite directions of polarization. The guides may also act as the spacers. In one embodiment, the guides may consist of 500 micron thick spacers for 400 micron thick magnets.

During assembly, the currents in the traces drive a magnet such as 32 into the guide rail 24 and down towards the mechanical stop 26. The magnet 32 encounters magnets 30 and 20 and connects to them magnetically, forming a microrobot. Once the microrobot has the desired number of magnets, the system drives out of the incubator area as shown by the outgoing arrow. One embodiment forms a microrobot of magnets of 1.4 mm by 1.4 mm by 0.4 mm magnets controllable in three or more degrees of freedom. Microrobots of greater complexity can be formed with additional magnets, end effectors, etc.

Figure 3:
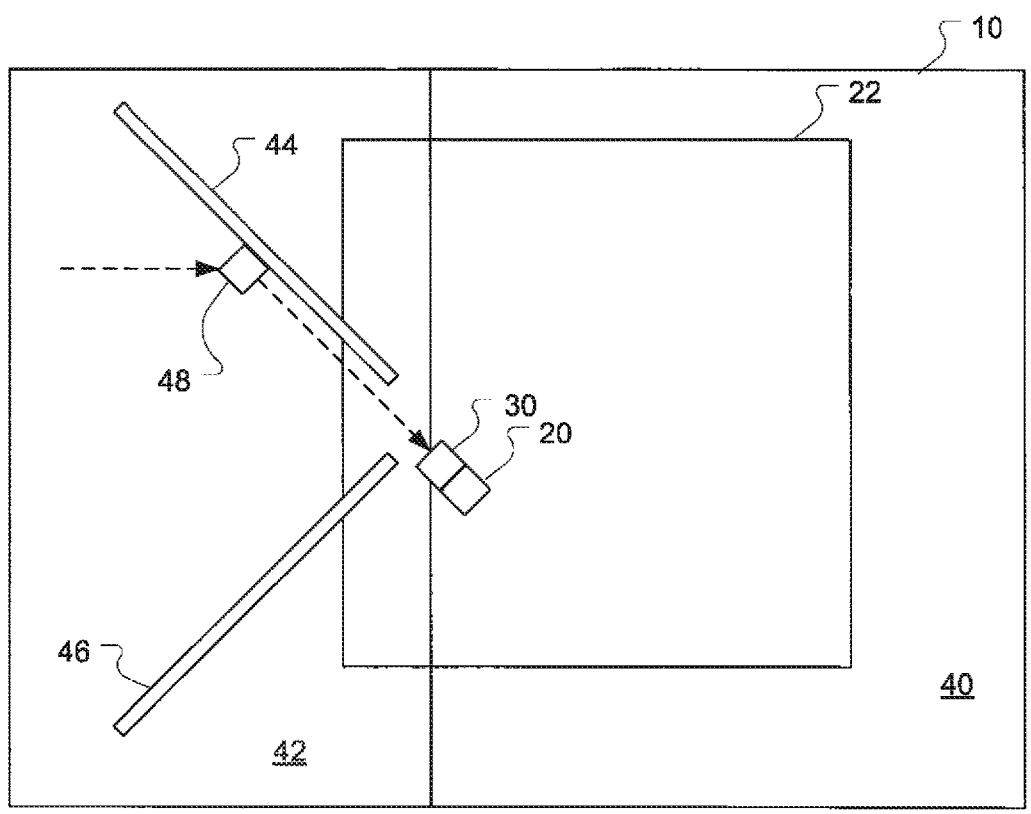
FIGS. 3-4 show a top view of an embodiment of a microrobot assembly system.
Figure 4:
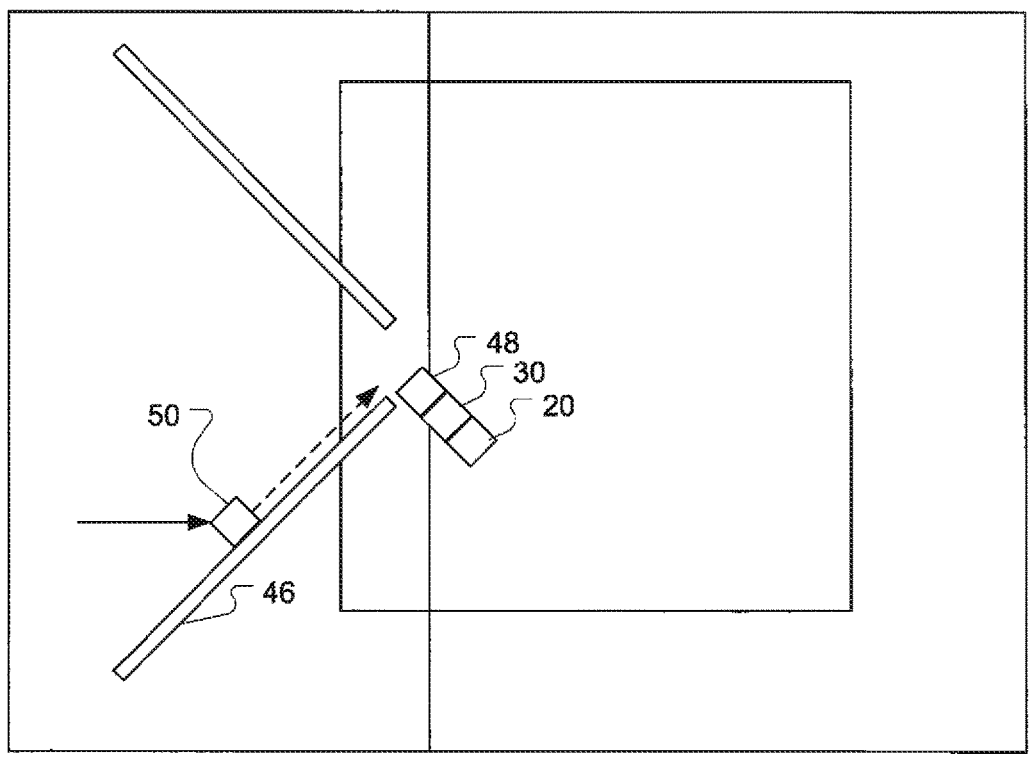

FIGS. 3 and 4 show view of an alternative embodiment. This embodiment also includes the substrate 10, the plate 22. Spacers, not shown in FIGS. 3 and 4, can hold the plate 22 the desired offset from the substrate 10. In this embodiment the conductive traces within the substrate, which provide the electrically controllable magnetic forces when driven with electrical current, are divided into independently controlled zones such as 40 and 42. In this embodiment the zone 40 constitutes a holding zone, and zone 42 a moving zone. In some embodiments with suitable magnet sizes (such as 1.4×1.4×0.4 mm magnets) plate 22 can be eliminated if the geometry is stable enough to prevent flipping one magnet on top of another. However, plate 22 generally increases reliability as subtle variations in magnets or surface interactions over time during motion may cause a flip. Zone 40 can also move magnets and magnetic arrays using its conductive traces, but it is referred to as a holding zone because during assembly its primary function is to hold the magnets in position. A starting structure, such as a 2×1 array to a position near the boundary between zone 40 and the zone 42, but still within the holding zone 40. By keeping some parts of the starting structure within the holding zone, the magnetic forces exerted by holding zone 40 may provide sufficient holding against the impact of incoming magnets.

As shown in FIGS. 3 and 4, the guides 44 and 46 provide direction to the magnets to form the new microrobot. In this embodiment, the starting structure consists of magnets 20 and 30 and magnet 48 is to be added to the structure. The magnet 48 is driving into the guide 44 and then along the guide 44 to magnetically attach to the starting structure. As shown in FIG. 4, the magnet could also be driven along the guide 46 into the structure that now consists of magnets 48, 30 and 20. One should note that the guides 44 and 46 may both be used or only one. If the adding magnet or other added structure are well controlled, the guides may not be needed. Once assembled, the microrobot drives out of the holding zone and into the moving zone.

Figure 5:
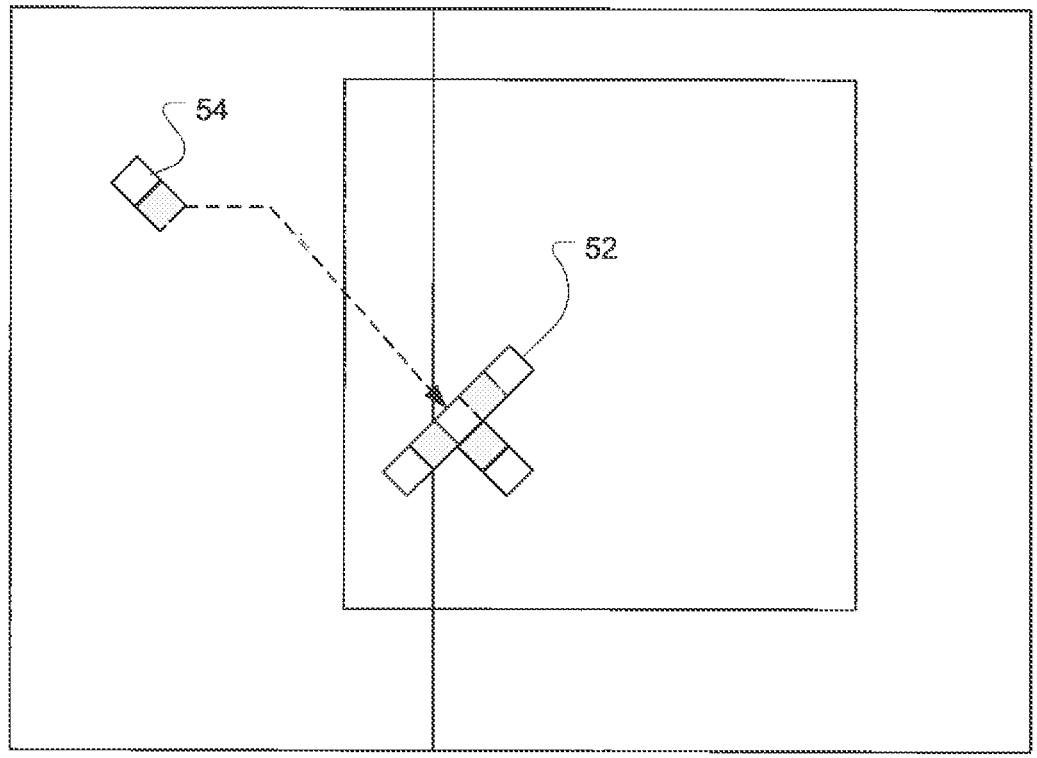
FIG. 5 shows a top view of an embodiment of a microrobot assembly system.

FIG. 5 shows an assembly system in which multiple magnets can be assembled at once rather than individually. This also increases the controllable assembly force. The structure 52 has alternating pole magnets. The gray magnets are magnets with north poles up and the white magnets are south poles up. The structure 52 has two north poles adjacent to the south pole where the structure 54 is to be added. This causes an energy barrier that must be overcome to push a north pole magnet against the 2 nearby north poles before it can snap to the south pole magnet. In some systems, the driving force may be insufficient to achieve this with a single magnet, but using two or more magnets in structure 54 may create enough force. In this manner, magnets can assemble into microrobots. In addition, microrobots can form themselves into microrobot trains.

Similar to microrobots that need extra force to snap to other structures, some applications may need enough force to perform certain tasks. In one example, the microrobots may need more force to insert an end effector into tissue such as to perform a biopsy or other such task. One should note that while this particular application involves an insertable application along a catheter, these are merely examples and are not intended to limit the scope of the embodiments.

Figure 6:
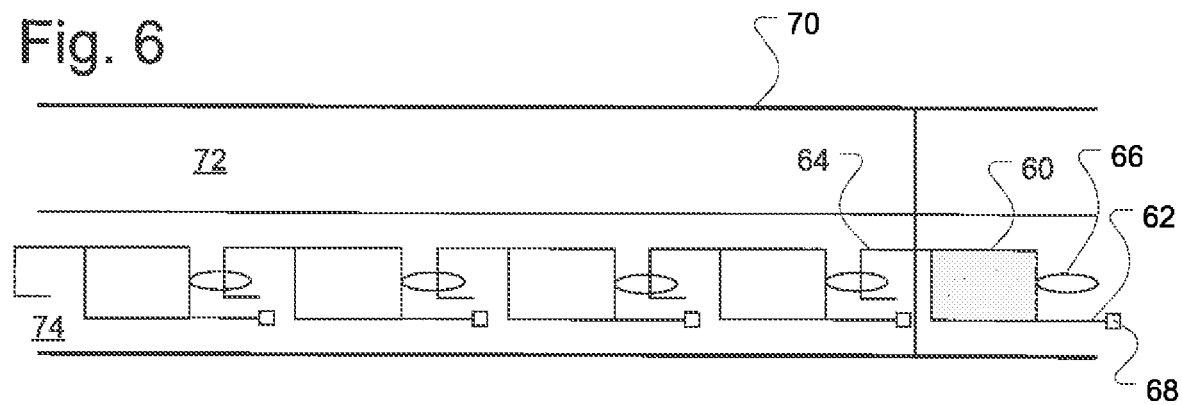
FIGS. 6-8 show an embodiment of a microrobot train assembly and application system.

In FIG. 6, a catheter 70 would have a flex circuit, not shown, similar to the substrate and traces shown in FIG. 1. The catheter has sufficient room to allow two paths, a forward path 74 and a return path 72. A first microrobot 60 has a front connector 66 and a rear connector 64. The microrobot 60 also has an end effector arm 62 and a tool 68. The tool 68 may consist of a needle, retrieval end effector, or other type of biopsy tool.

Figure 7:
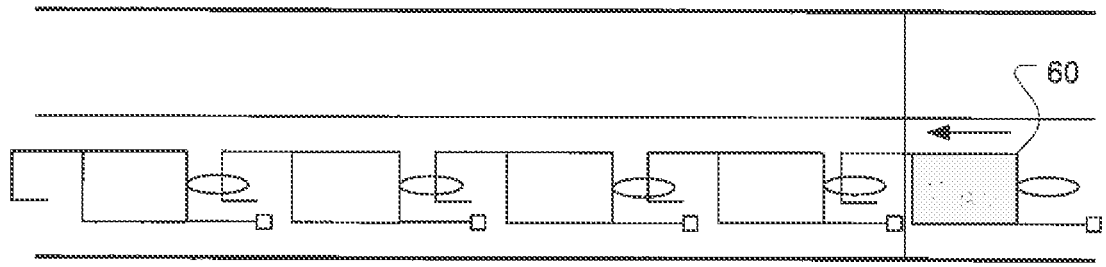
Figure 8:
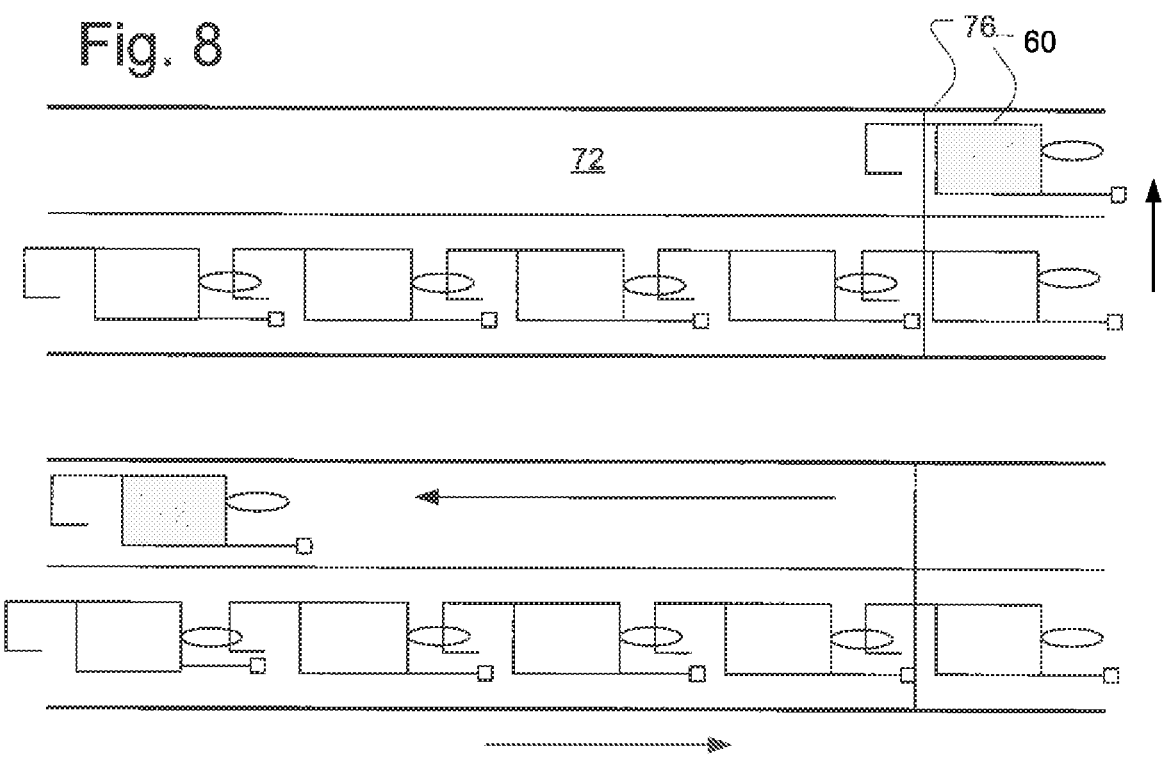

The microrobot 60 forms a train with other microrobots by means of the front and back connectors. The connectors in this embodiment consist of an eye loop 66 and a hook 64. Connectors may also be magnetic or other means known in the prior art of small connectors. The microrobots can connect themselves together to form the train. FIG. 7 shows an example of how one microrobot can disconnect itself from the train. By moving slight backwards, as shown in FIG. 7, the hook releases from the eye loop. As shown in FIG. 8, the microrobot 60 then moves up to the return path 72 and the remainder of the train then moves up into the space previously occupied by microrobot 60. This allows the system to replace one robot and one robot function with another very quickly, without withdrawing the entire instrument from the catheter each time.

With the mechanically linked robots, the combined microrobots can achieve a higher force than they can individually. The amount of force needed the number of microrobots needed in the train, based on the amount of force each microrobot can exert individually to add to the total train force. The region 76 of the forward and return paths 72 forms a control zone with multiple degrees of freedom. One variation would be to have multiple microrobots in the return path.

In addition to microrobot trains that can have biopsy end effectors, some end effectors use wetting to perform pick and place of items. One embodiment performs pick and place of small pieces of material, referred to as platelets. Issues arise with using wetting. Simple wetting surface can work, but dry out relatively quickly, and it is not easy to determine whether or not they have liquid. In addition, other surfaces are rigid and then do not wet the pick object as well as desired for reliable gripping.

Figure 9:
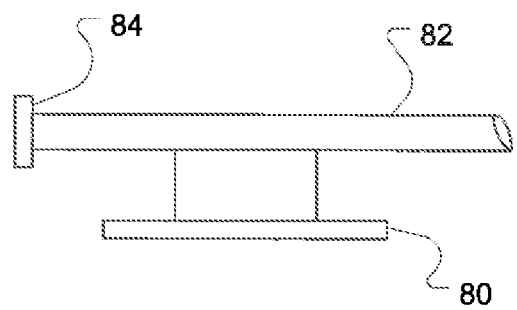
FIG. 9 shows an embodiment of a wetting end effector.

An embodiment of an end effector that achieves more reliable wetting and has easily determinable liquid levels is shown in FIG. 9. The microrobot 80 has a capillary 82 that acts as a reservoir of liquid and will typically be transparent to allow one to determine the amount of liquid in the reservoir as well as being easily fillable. In one preferred embodiment, the capillary 82 was a polyimide capillary with a diameter of 1.5 mm and length of 5-10 mm. The capillary length is normally chosen so that the liquid stays in the capillary (in liquid communication with end effector 84) in all robot orientations. In another preferred embodiment, the length is chosen relative to the diameter so that liquid is held in while the microrobot is in a horizontal orientation, but drops come out when the microrobot is tilted vertically, such as while operating on a flex circuit known in the prior art. In this preferred embodiment, the microrobot can therefore dispense liquid drops on demand, such as for watering plants or other automation functions where drop dispensing is desired.

The capillary reservoir also allows the microrobot to pick and place multiple objects before needing to be refilled. The end effector may be porous or other absorptive material that can absorb liquids from the reservoir. These materials also provide a slight negative pressure relative to atmosphere on the liquid relative to atmosphere due to wetting of a large surface. This slight negative pressure prevents excessive water from flowing, such as on the object being picked up. The end effector 84 may consist of metal meshes, porous materials such as porous polyethylene, sponges, brushes, hydrogels and other high surface area wetting surfaces.

In this manner, one can assemble microrobots from magnets, and microrobot trains from multiple microrobots. The configuration of the microrobots and the microrobot trains depends upon the desired application. For example, the configuration of the microrobots may depend upon the size desired, or the number of poles desired. The configuration of the trains may depend upon the desired amount of force to be applied to a surface. The end effector used may include a porous or other absorptive material attached to a capillary that acts a reservoir of liquid.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed is:

1. A microrobot assembly system, comprising:
   a substrate containing at least one conductive trace;
   a diamagnetic layer on the substrate;
   at least one spacer on the diamagnetic layer having a predetermined height;
   a plate on the at least one spacer; and
   at least two magnets movable across the diamagnetic layer when voltage is applied to the at least one conductive trace, the magnets having a height less than the predetermined height.

2. The assembly system of claim 1, wherein the plate comprises one of copper, aluminum and glass.

3. The assembly system of claim 1, wherein the plate is spaced above the diamagnetic layer a predetermined height.

4. The assembly system of claim 1, wherein the at least one conductive trace comprises at least one conductive trace formed into two control zones, a holding zone and a moving zone.

5. The assembly system of claim 4, wherein the plate is on the diamagnetic layer adjacent a boundary between the two control zones.

6. The assembly system of claim 5, further comprising at least one guide arranged to direct the magnets from the moving zone to the holding zone.

7. The assembly system of claim 4, wherein the at least two magnets comprise at least three magnets movable into the holding zone to form one of a one-dimensional array and a two-dimensional array.

8. The assembly system of claim 1, further comprising a mechanical stop.

9. The assembly system of claim 8, further comprising a guide arranged adjacent the mechanical stop.

10. The assembly system of claim 9, wherein the guide comprises the at least one spacer.

11. A microrobot assembly system, comprising:
    a substrate containing conductive traces formed into at least one holding zone and one moving zone;
    a diamagnetic layer on the substrate; and
    at least two magnetic structures movable across the diamagnetic layer in response to voltages applied to the conductive traces, wherein the holding zone holds one of the magnetic structures and the moving zone allows another of the magnetic structures to attach to the magnetic structure being held.

* * * * *